(12) United States Patent
Murashima et al.

(10) Patent No.: US 11,965,857 B2
(45) Date of Patent: Apr. 23, 2024

(54) CARBON-BASED MATERIAL VIBRATOR, A SENSOR ELEMENT HAVING THE SAME, AND A BIOLOGICAL SUBSTANCE DETECTION DEVICE HAVING THE SAME

(71) Applicants: KANEKA CORPORATION, Osaka (JP); OSAKA UNIVERSITY, Osaka (JP)

(72) Inventors: Kensuke Murashima, Osaka (JP); Mutsuaki Murakami, Osaka (JP); Hirotsugu Ogi, Osaka (JP); Koichi Kusakabe, Osaka (JP)

(73) Assignees: KANEKA CORPORATION, Osaka (JP); OSAKA UNIVERSITY, Osaka (JP)

( * ) Notice: Subject to any disclaimer, the term of this patent is extended or adjusted under 35 U.S.C. 154(b) by 478 days.

(21) Appl. No.: 17/222,324

(22) Filed: Apr. 5, 2021

(65) Prior Publication Data
US 2021/0223212 A1 Jul. 22, 2021

Related U.S. Application Data

(63) Continuation of application No. PCT/JP2019/039111, filed on Oct. 3, 2019.

(30) Foreign Application Priority Data

Oct. 5, 2018 (JP) .................. 2018-190405

(51) Int. Cl.
*G01N 29/00* (2006.01)
*G01N 29/12* (2006.01)
(Continued)

(52) U.S. Cl.
CPC ......... *G01N 29/12* (2013.01); *G01N 29/2418* (2013.01); *G01N 33/483* (2013.01); *G01N 2291/0256* (2013.01)

(58) Field of Classification Search
CPC ........ G01N 29/00; G01N 29/02; G01N 29/12; G01N 29/2418; G01N 33/48; G01N 33/483; G01N 2291/0256
See application file for complete search history.

(56) References Cited

U.S. PATENT DOCUMENTS

2010/0173422 A1   7/2010  Koley et al.
2020/0225221 A1*  7/2020  Nahm .................. G01N 33/551

FOREIGN PATENT DOCUMENTS

JP    2003172737 A   6/2003
JP    2010185772 A   8/2010
JP    2017156253 A   9/2017

OTHER PUBLICATIONS

International Search Report issued in corresponding International Application No. PCT/JP2019/039111, dated Dec. 24, 2019, with translation (5 pages).

(Continued)

*Primary Examiner* — Nguyen Q. Ha
(74) *Attorney, Agent, or Firm* — Osha Bergman Watanabe & Burton LLP

(57) ABSTRACT

A vibrator that is capable of vibrating without using an electrode and has good detection sensitivity is provided. A carbon-based material vibrator for vibration by light irradiation has a biological substance or a substance capable of identifying a biological substance immobilized on the vibrator. The vibrator may not include a counter electrode for applying a voltage to the vibrator. The carbon-based material may be graphite. A thermal conductivity $\lambda 1$ in a plane direction of the carbon-based material is 100 times or more than a thermal conductivity $\lambda 2$ in a thickness direction of the carbon-based material.

10 Claims, 3 Drawing Sheets

(51) Int. Cl.
*G01N 29/24* (2006.01)
*G01N 33/48* (2006.01)
*G01N 33/483* (2006.01)

(56) References Cited

OTHER PUBLICATIONS

Written Opinion issued in corresponding International Application No. PCT/JP2019/039111, dated Dec. 24, 2019 (5 pages).

* cited by examiner

CARBON-BASED MATERIAL VIBRATOR, A SENSOR ELEMENT HAVING THE SAME, AND A BIOLOGICAL SUBSTANCE DETECTION DEVICE HAVING THE SAME

CROSS REFERENCE TO RELATED APPLICATIONS

The present application claims the benefits of the priority of Japanese Patent Application No. 2018-190405 filed on Oct. 5, 2018. The entire contents of the specification of Japanese Patent Application No. 2018-190405 filed on Oct. 5, 2018 are incorporated by reference herein.

TECHNICAL FIELD

The present disclosure relates to a carbon-based material vibrator, a sensor element having the same, and a biological substance detection device having the same.

BACKGROUND

Conventional biosensors utilize a reaction of a biological substance such as an antigen, an enzyme, a hormone, and DNA with a specific substance to detect the reaction as a physical change, a thermal change, a chemical change, or the like.

For example, Patent Document 1 discloses a sensor element including a substrate and a metal thin film. The metal thin film is formed on the substrate and has a surface on which a protein to complement an object to be detected is immobilized, and vibrates by irradiation with laser light.

Patent Document 2 discloses a biosensor in which a physiologically active substance is immobilized on a substrate. The substrate comprises a solid support. A surface of the solid support is chemically modified and the solid support is obtained by forming a surface treatment layer on a crystal oscillator which is an element having an electromechanical conversion function. The surface treatment layer is diamond, diamond-like carbon, or the like.

PATENT LITERATURE

Patent document 1: JP2010-185772A
Patent document 2: JP2003-172737A

Patent Document 1 is directed to a resonance vibrator mass detector using a conventional piezoelectric vibrator. It is difficult to reduce the thickness of the piezoelectric vibrator below several tens of μm and to keep mechanical strength, resulting in low sensitivity of the resonance vibrator mass detector. Patent Document 1 describes that a first metal thin film is formed on the substrate, so that the film thickness of the first metal thin film can be reduced. However, according to the studies of the inventors, in a biosensor that detects a biological substance from a change in resonance frequency of a vibrator as in Patent Document 1, the biosensor using the metal thin film disclosed in Patent Document 1 still has room for improvement in persistence of vibration. Furthermore, on the metal thin film, which has high thermal conductivity, a protein or the like immobilized thereon may be deactivated due to a heat rise by laser irradiation. Therefore, it is not desirable to extremely reduce the thickness of the metal thin film, resulting in limit of sensitivity. In Patent Document 2, an electrode is formed in the crystal oscillator as a piezoelectric vibrator. However, considering time and cost of electrode formation, a vibrator capable of vibrating without using an electrode is desired.

Therefore, one or more embodiments of the present disclosure are directed to a vibrator that is capable of vibrating without using an electrode and has good persistence of vibration. The vibrator of one or more embodiments of the present invention advantageously further has good detection sensitivity and does not cause damage to immobilized protein or the like.

SUMMARY

One or more embodiments of the present invention are as follows.

[1] A carbon-based material vibrator for vibration by light irradiation, wherein a biological substance or a substance capable of identifying a biological substance is immobilized on the vibrator.

[2] The vibrator according to [1], wherein the vibrator does not comprise a counter electrode for applying a voltage to the vibrator.

[3] The vibrator according to [1] or [2], wherein the carbon-based material is graphite.

[4] The vibrator according to any one of [1] to [3], wherein a thermal conductivity $\lambda 1$ in a plane direction of the carbon-based material is 100 times or more a thermal conductivity $\lambda 2$ in a thickness direction of the carbon-based material.

[5] A sensor element comprising the vibrator according to any one of [1] to [4] and a holding member.

[6] The sensor element according to [5], further comprising a microchannel.

[7] A biological substance detection device comprising:
the vibrator according to any one of [1] to [4];
a holding member to hold the vibrator;
a microchannel through which a specimen flows into the vibrator;
a pump light source irradiating the vibrator with a pump light to vibrate the vibrator;
a probe light source irradiating the vibrator vibrated by the pump light with a probe light; and
a detector measuring a vibration displacement of the vibrator on a basis of a reflectance of a probe light reflected by the vibrator to detect a biological substance.

The vibrator of one or more embodiments of the present invention can be vibrated by light irradiation, even without using an electrode like a piezoelectric vibrator, and allows the vibration to persist for a long time. Furthermore, in one or more embodiments of the present invention, since a thermal conductivity in the out-of-plane direction is low, a heat flow generated by light irradiation escapes mainly in the in-plane direction, and the influence of heating on protein or the like immobilized on the surface is significantly reduced, so that the deactivation of the protein or the like can be prevented. As a result, in one or more embodiments of the present invention, the thickness of the vibrator can be further reduced, and the detection sensitivity can be significantly improved.

DETAILED DESCRIPTION

Figure 1:
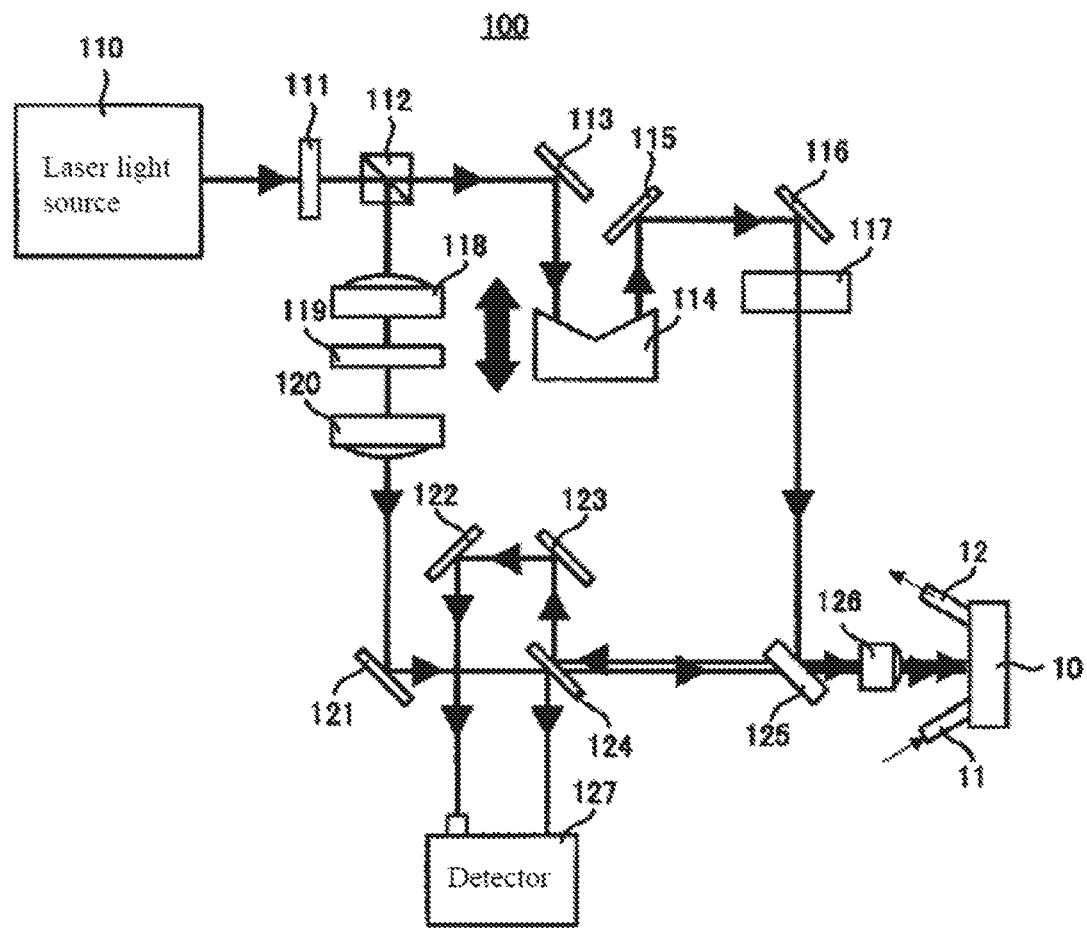
FIG. 1 is a schematic view showing an example of a biological substance detection device of one or more embodiments of the present invention.

One or more embodiments of the present disclosure are directed toward a carbon-based material vibrator on which a biological substance or a substance capable of identifying a biological substance is immobilized, and the carbon-based material vibrator is vibrated by light irradiation. In one or more embodiments, the carbon-based material vibrator of the present disclosure does not have a counter electrode for applying a voltage to the vibrator, which a piezoelectric vibrator usually has.

In one or more embodiments, the carbon-based material may contain a carbon atom as a constituent component, and may be an amorphous carbon material, a crystalline carbon material, or a metal carbide.

In one or more embodiments, examples of the amorphous carbon material may include amorphous carbon and diamond-like carbon. Diamond-like carbon is an amorphous carbon material in which carbon having an $sp^3$ bond and carbon having an $sp^2$ bond coexist irregularly. Examples of amorphous carbon may include amorphous carbon obtained by heat-treating a polymer film such as aromatic polyimide at about 900 to 1000° C. in an inert gas atmosphere. In such amorphous carbon, the total ratio of oxygen and nitrogen is usually 10% by mass or more and 30% by mass or less. Examples of the crystalline carbon material may include graphite. Examples of the metal carbide may include molybdenum carbide, tungsten carbide, and titanium carbide. The carbon-based material is preferably graphite. Since a mass density of a graphite vibrator is sufficiently smaller than a mass density of metal and also smaller than mass densities of other carbon materials, the graphite vibrator has good mass detection sensitivity for a target biological substance and can suppress damage to a biological substance or a substance capable of identifying a biological substance. In addition, since the graphite vibrator has the advantage of being high in strength as a self-supported film, the graphite vibrator can be used as a vibrator even without a substrate, and can improve the persistence of vibration, which can be evaluated by a Q-value, or the like, of vibration.

In one or more embodiments, by subjecting a carbon-based material to laser Raman measurement, the ratio of amorphous carbon to graphite therein can be determined. When the carbon-based material in one or more embodiments of the present invention is measured by laser Raman spectroscopy, a G-band caused by a graphite structure appears in the vicinity of 1575 to 1600 $cm^{-1}$, and a D-band caused by an amorphous carbon structure appears in the vicinity of 1350 to 1360 $cm^{-1}$. In one or more embodiments of the present invention, a carbon-based material having a ratio (I(D)/I(G)) of an intensity I(D) of the D-band to an intensity I(G) of the G-band of 0 or more and 0.7 or less is referred to as graphite. The I(D)/I(G) of graphite is preferably 0 or more and 0.5 or less, more preferably 0 or more and 0.1 or less, and particularly preferably 0 or more and 0.05 or less. A vibrator composed of graphite having an I(D)/I(G) of 0.5 or less is preferable because such a vibrator has a low mass density and therefore has good detection sensitivity for a biological substance. Moreover, in such a vibrator, the out-of-plane thermal conductivity is sufficiently smaller than the in-plane thermal conductivity, and thus heating by light irradiation of the back surface does not exert the influence on a biological substance to be detected on the front surface, and damage to the biological substance can be suppressed.

The shape of the carbon-based material constituting the vibrator of one or more embodiments of the present invention is not particularly limited, and the carbon-based material may be, for example, a film in the shape of polygon such as square and rectangle, or a film in the shape of circle, ellipse, or the like. The area of the vibrator may be, for example, 4 $mm^2$ or more and 400 $mm^2$ or less. In one or more embodiments, the thickness of the carbon-based material is preferably 10 nm or more. By allowing the thickness of the carbon-based material to be 10 nm or more, it is possible to reduce damage (deactivation) caused by pulsed light to a biological substance or a substance capable of identifying a biological substance immobilized on the carbon-based material vibrator, and a target biological substance to be detected. The thickness of the carbon-based material is more preferably 20 nm or more, further preferably 30 nm or more, and still more preferably 50 nm or more. The upper limit of the thickness of the carbon-based material is, for example, 1000 nm or less. When a biological substance is detected, particularly by using a resonance method described later, the thickness of the carbon-based material is preferably 500 nm or less. When the thickness of the carbon-based material is 500 nm or less, it is possible to cause resonance of the vibrator without generating elastic pulse waves having aligned phases in the vibrator. The thickness of the carbon-based material is more preferably 200 nm or less, and still more preferably 100 nm or less.

In one or more embodiments of the present invention, when the carbon-based material is graphite, the orientation in the c-axis direction of crystallites in graphite can be evaluated by a mosaic spread. The mosaic spread can be measured using an X-ray diffraction apparatus. First, a counter (2θ axis) of the X-ray diffraction apparatus is fixed at a position showing the peak of the X-ray diffraction line of (002) plane of a plate-shaped graphite film. Then, only a sample (θ axis) is rotated, and an intensity function (a sample azimuth-dependent curve of peak intensity of the (002) plane diffraction line) is measured. A half value of peak intensity is determined from the obtained intensity function, and this half value of peak intensity is defined as a mosaic spread.

A lower value of mosaic spread indicates higher orientation in the c-axis direction. When a value of mosaic spread is large, namely when the orientation in the c-axis direction of crystallites in graphite is low, connected bodies of 6-membered rings may align irregularly in the c-axis direction, and graphite is apt to become brittle. For example, a mosaic spread of 0.3° indicates that deviation of the c-axis from the direction vertical to a connected body (plate surface) of 6-membered rings is within approximately ±0.6° ("Carbon Yogo-Jiten (Terminological Dictionary on Carbon Materials)", edited by Yasuda Keiichi and Kobayashi Kazuo of the editorial committee for "Carbon Yogo-Jiten" of The Carbon Society of Japan, Agne Shofu Publishing Inc., 2000). In one or more embodiments, the mosaic spread of graphite is preferably 3.0° or less, more preferably 1.5° or less, and further preferably 0.5° or less. When the mosaic spread is 5.0° or less, there is an advantage that graphite can be superior in heat dissipation performance. In one or more embodiments, the lower limit of the mosaic spread is 0.1° or more. The mosaic spread can be regulated by temperature or pressure during a firing process in producing graphite.

In one or more embodiments, the thermal conductivity $\lambda 1$ in the plane direction of the carbon-based material is preferably 100 times or more than the thermal conductivity $\lambda 2$ in the thickness direction of the carbon-based material. When the thermal conductivity $\lambda 1$ in the plane direction is sufficiently greater than the thermal conductivity λ2 in the thickness direction, heat generated in the vibrator by light irradiation can be restrained from conducting in the thickness direction of the vibrator, and the heat escapes in the in-plane direction. As a result of this, the deactivation of a biological substance, or a substance capable of identifying a biological substance immobilized on the vibrator on the surface opposite to the light irradiation surface and a target biological substance to be detected, can be suppressed. In one or more embodiments, the ratio of the thermal conductivity λ1 in the plane direction to the thermal conductivity λ2 in the thickness direction of the carbon-based material is more preferably 200 times or more, and the upper limit thereof is not particularly limited, but is, for example, 300 times.

When a biological substance adhering to the vibrator is detected from a change in resonance frequency of the vibrator as a mass addition, the detection sensitivity is inversely proportional to the density of the vibrator and inversely proportional to the square of the thickness of the vibrator. In one or more embodiments, by using the carbon-based material as a vibrator, the detection sensitivity is increased by 10 times or more as compared with the detection sensitivity in the case of using a conventional metal. The carbon-based material preferably has a density of 2.26 $g/cm^3$ or less, and more preferably 2.2 $g/cm^3$ or less. The lower limit of the density may be, for example, 2.0 $g/cm^3$.

When the vibrator of one or more embodiments of the present invention is a diamond-like carbon vibrator, the diamond-like carbon vibrator can be produced by a physical vapor deposition method (a sputtering method, an arc ion plating method, an ion deposition method, and the like) using solid carbon as a raw material, or a chemical vapor deposition method (a plasma CVD method, a thermal CVD method, an optical CVD method, and the like) using a hydrocarbon gas as a raw material.

When the vibrator of one or more embodiments of the present invention is an amorphous carbon vibrator, the amorphous carbon vibrator can be produced by, for example, a physical vapor deposition method such as a vacuum vapor deposition method, or a method of preparing amorphous carbon by subjecting a polymer film such as aromatic polyimide to a carbonization heat treatment. The carbonization heat treatment may be carried out at about 900 to 1000° C. for 15 to 30 minutes in an atmosphere of an inert gas such as nitrogen, argon, or a mixed gas of argon and nitrogen.

When the vibrator of one or more embodiments of the present invention is a graphite vibrator, the graphite vibrator can be produced, for example, by the following method: a polymer film such as aromatic polyimide is subjected to a carbonization heat treatment to obtain an amorphous carbon film, and the amorphous carbon film is placed in a high-temperature furnace and subjected to a graphitization heat treatment of heat-treating (firing) at 2200° C. or higher (preferably 2600° C. or higher) in an inert gas such as argon gas or a mixed gas of argon gas and helium gas for 15 to 30 minutes. The heat treatment temperature in graphitization is more preferably 2800° C. or higher, and further preferably 3000° C. or higher, and the upper limit thereof is not particularly limited, but is, for example, 3600° C. or lower.

In one or more embodiments, a polymer preferably used as a raw material for an amorphous carbon vibrator or a graphite vibrator is an aromatic polymer. The aromatic polymer is preferably at least one polymer selected from polyamides, polyimides, polyquinoxaline, polyparaphenylene vinylene, polyoxadiazole, polybenzimidazole, polybenzoxazole, polybenzthiazole, polyquinazolinedione, polybenzoxazinone, polyquinazolone, benzimidazobenzophenanthroline ladder polymer, and derivatives of these polymers. A film made of these polymers may be produced by a known production method. As particularly preferable polymers, aromatic polyimides, polyparaphenylene vinylene, and polyparaphenylene oxadiazole can be exemplified. In particular, aromatic polyimides are preferable, and an aromatic polyimide produced from a polyamide acid obtained from an acid dianhydride (in particular, an aromatic acid dianhydride) and a diamine (in particular, an aromatic diamine) as described below is particularly preferable.

Examples of the acid dianhydride which can be used in a synthesis of the aromatic polyimide include pyromellitic dianhydride, 2,3,6,7-naphthalenetetracarboxylic dianhydride, 3,3',4,4'-biphenyltetracarboxylic dianhydride, 1,2,5,6-naphthalenetetracarboxylic dianhydride, 2,2',3,3'-biphenyltetracarboxylic dianhydride, 3,3',4,4'-benzophenonetetracarboxylic dianhydride, 2,2-bis(3,4-dicarboxyphenyl)propane dianhydride, 3,4,9,10-perylenetetracarboxylic dianhydride, bis(3,4-dicarboxyphenyl)propane dianhydride, 1,1-bis(2,3-dicarboxyphenyl)ethane dianhydride, 1,1-bis(3,4-dicarboxyphenyl)ethane dianhydride, bis(2,3-dicarboxyphenyl)methane dianhydride, bis(3,4-dicarboxyphenyl)ethane dianhydride, oxydiphthalic dianhydride, bis(3,4-dicarboxyphenyl)sulfone dianhydride, p-phenylenebis(trimellitic acid monoester acid anhydride), ethylene bis(trimellitic acid monoester acid anhydride), bisphenol A bis(trimellitic acid monoester acid anhydride), and analogues thereof. These can be used singly or in mixture at arbitrary proportions. Pyromellitic dianhydride and 3,3',4,4'-biphenyltetracarboxylic dianhydride are particularly preferable from the viewpoint that the orientation of the polyimide film is higher as the polyimide film has a polymer structure with a significantly rigid structure and the viewpoint of availability.

Examples of the diamine which can be used in a synthesis of the aromatic polyimide include 4,4'-diaminodiphenylpropane, 4,4'-diaminodiphenylmethane, benzidine, 3,3'-dichlorobenzidine, 4,4'-diaminodiphenyl sulfide, 3,3'-diaminodiphenyl sulfone, 4,4'-diaminodiphenyl sulfone, 4,4'-diaminodiphenyl ether, 3,3'-diaminodiphenyl ether, 3,4'-diaminodiphenyl ether, 1,5-diaminonaphthalene, 4,4'-diaminodiphenyldiethylsilane, 4,4'-diaminodiphenylsilane, 4,4'-diaminodiphenylethylphosphine oxide, 4,4'-diaminodiphenyl N-methylamine, 4,4'-diaminodiphenyl N-phenylamine, 1,4-diaminobenzene(p-phenylenediamine), 1,3-diaminobenzene, 1,2-diaminobenzene, and analogues thereof. These can be used singly or in mixture at arbitrary proportions. Furthermore, from the viewpoint of enhancing an orientation of the polyimide film and the viewpoint of availability, it is particularly preferable to synthesize the aromatic polyimide using 4,4'-diaminodiphenyl ether or p-phenylenediamine as raw materials.

In one or more embodiments, when the polymer is an aromatic polyimide, there are the following methods to produce the aromatic polyimide: a thermal curing method in which a polyamic acid as a precursor is converted to an imide by heating; and a chemical curing method in which a polyamic acid is converted to an imide using a dehydrating agent typified by an acid anhydride such as acetic anhydride, and a tertiary amine such as picoline, quinoline, isoquinoline, and pyridine as an imidization accelerating agent. Either of these methods may be used. The chemical curing method is preferable from the viewpoint that the film to be obtained has a small coefficient of linear expansion, a high elastic modulus, and a high birefringence, and is not fractured even if tension is applied thereto during the firing of the film, and high-quality graphite can be obtained. The chemical curing method is also excellent from the perspective of improving the thermal conductivity of a graphite film.

In one or more embodiments, at least one acid dianhydride and at least one diamine are dissolved in an organic solvent to obtain an organic solvent solution of polyamic acid, and the organic solvent solution of polyamic acid is stirred under a controlled temperature condition until a polymerization of the acid dianhydride and the diamine is completed to prepare a polyamic acid. Such a polyamic acid solution is obtained usually at a concentration of 4% by mass or more (preferably 5% by mass or more) and 35% by mass or less, and preferably 10% by mass or more and 30% by mass or less. A polyamic acid solution at a concentration falling within the above range can have a suitable molecular weight and a suitable solution viscosity. The acid dianhydride and the diamine in the above raw material solution are preferably set to be in substantially equimolar amounts. A molar ratio of the acid dianhydride to the diamine (acid dianhydride/diamine) is, for example, 1.5/1 or less and 1/1.5 or more, preferably 1.2/1 or less and 1/1.2 or more, and more preferably 1.1/1 or less and 1/1.1 or more.

In one or more embodiments, the polyimide film is produced by casting an organic solvent solution containing the polyamide acid, as the precursor of the polyimide, onto a support such as an endless belt or a stainless steel drum, and drying and imidizing the solution. A specific production method of the film by the chemical curing method is as follows. First, a stoichiometric amount or more of a dehydrating agent and a catalytic amount of an imidization accelerating agent are added to the above solution of polyamic acid, the mixture is cast or applied onto a support plate, an organic film such as PET, or a support such as a drum or an endless belt to be formed into a film shape, and the organic solvent is evaporated to obtain a film having a self-supporting property. Subsequently, this film is imidized while being further heated and dried to obtain a polyimide film. A temperature at the time of heating is preferably in a range of 150° C. to 550° C. The thickness of the polymer film is preferably, for example, 30 to 3000 nm.

When the vibrator of one or more embodiments of the present invention is a metal carbide vibrator, the metal carbide vibrator can be produced by physical vapor deposition of a solid raw material of metal carbide using an ion plating method or the like, or by chemical vapor deposition of a mixed gas of a hydrocarbon gas and a gas containing a metal atom as a constituent using a plasma CVD method or the like. The term "metal" used in the present specification is intended to also include a semimetal such as Si.

On the carbon-based material vibrator of one or more embodiments of the present invention, a biological substance or a substance capable of identifying a biological substance by bonding to the biological substance (hereinafter, these may be collectively referred to as a substance having a bio-identifying property) may be immobilized. These substances form strong specific or complementary binding to each other, and therefore, when one of the substances is immobilized on the carbon-based material vibrator, the other substance in a specimen can also be bonded to the carbon-based material vibrator, and the type and amount of the other substance in the specimen can be measured.

Examples of a combination of a biological substance and a substance capable of identifying a biological substance include a combination of an antibody or a part thereof (for example, a site including a variable region such as a light chain, a Fab region, or the like) and an antigenic substance, a combination of proteins or polypeptides both of which can identify with each other by binding, a combination of an enzyme and a substrate capable of forming a complex with the enzyme, a combination of a hormone receptor and a hormone, and a combination of a nucleic acid such as oligonucleotide or a part thereof and another nucleic acid or a part thereof capable of complementarily binding to the nucleic acid or a part thereof. Among these, it is preferable to bind an antibody or a part thereof (in particular, a light chain or a Fab region) to the carbon-based material vibrator.

In one or more embodiments, to bond the substance having a bio-identifying property to a carbon-based material film to obtain a carbon-based material vibrator, for example, a group that can form a chemical bonding to the substance having a bio-identifying property (hereinafter referred to as a bonding group to the bio-identifying substance) may be introduced into the carbon-based material film. The bonding group to the bio-identifying substance may be allowed to react with the substance having a bio-identifying property. In order to introduce the bonding group to the bio-identifying substance into the carbon-based material film, for example, the following methods (1) to (3) can be adopted: (1) a method in which a carbon-carbon bond of the carbon-based material film is cleaved to introduce a polar group, and the polar group is used as it is as the bonding group to the bio-identifying substance, or the polar group is subjected to functional group conversion to be the bonding group to the bio-identifying substance; (2) a method in which a polar group or a converted group thereof is introduced in the same manner as in the above (1), and a substance A (hereinafter referred to as a linker A) having a group capable of reacting with the polar group or the converted group and the bonding group to the bio-identifying substance is allowed to react; and (3) a method in which a substance B (hereinafter referred to as a linker B) having a group that has an affinity for the carbon-based material film (hereinafter referred to as a carbon-affinity group) and the bonding group to the bio-identifying substance is allowed to act on the carbon-based material film.

Examples of a method for the introduction of the polar group by cleaving the carbon-carbon bond and the subsequent functional group conversion in the method (1) may include a method of irradiating the carbon-based material film with ultraviolet rays in chlorine gas to chlorinate its surface, a method of irradiating the chlorinated product with ultraviolet rays in ammonia gas to aminate it, a method of subjecting the carbon-based material film to plasma treatment in ammonia gas to aminate its surface, a method of treating the aminated surface with an acid chloride, an acid anhydride, or the like to carboxylate the surface, a method of actively esterifying the carboxylated surface with N-hydroxysuccinimide, p-nitrophenol, bis(pentafluorophenyl) carbonate, or the like, and a method of introducing a hydroxyl group, a carboxyl group, an epoxy group, an amino group, a thiol group, an isocyanate group, or the like by appropriately conducting functional group conversion.

In one or more embodiments, a compound having a group having reactivity with the polar group or the converted functional group and the bonding group to the bio-identifying substance can be used as the linker A used in the method (2). The group having reactivity with the polar group or the converted functional group is preferably a carboxylic acid group. The bonding group to the bio-identifying substance can be appropriately selected according to a substance having a bio-identifying property to be linked, and examples of the bonding group to the bio-identifying substance include a hydroxy group, a carboxyl group, an activated carboxyl group, an epoxy group, an amino group, a thiol group, and an isocyanate group. When the substance having a bio-identifying property is protein or polypeptide, the bonding group to the bio-identifying substance is preferably a group that can bind to an $NH_2$ bond at an N-terminal or a side chain of protein or polypeptide. Examples of such a group include a carboxylic acid group, a carboxylic acid halide group, and an activated ester group, and a carboxylic acid group and an activated ester group are preferred. Examples of the activated ester group include an active ester group formed from N-hydroxysuccinimide, an active ester group formed from p-nitrophenol, and an active ester group formed from bis(pentafluorophenyl) carbonate.

In one or more embodiments, the linker A is preferably a compound having a carboxylic acid group as a group having reactivity with the polar group or the converted functional group, and a carboxylic acid group as the bonding group to the bio-identifying substance, namely a polyvalent carboxylic acid compound. Examples of the polyvalent carboxylic acid include dicarboxylic acids such as oxalic acid, malonic acid, succinic acid, maleic acid, and fumaric acid, and trimellitic acid. These acids may be acid anhydrides. After a polyvalent carboxylic acid compound is bonded to the carbon-based material film at its one carboxylic acid group, the remaining carboxylic acid group may be converted to an activated ester group and then bonded to a substance having a bio-identifying property.

Examples of the carbon-affinity group of the linker B used in the method (3) include a group having one or more benzene rings, and in addition, include a condensed ring group such as a naphthalene ring, a biphenylene ring, an acenaphthylene ring, a phenalene ring, a phenanthrene ring, an anthracene ring, a fluoranthene ring, a triphenylene ring, a pyrene ring, a perylene ring, a coronene ring, a pyranthrene ring, and an ovalene ring. The condensed ring group preferably has 3 or more aromatic carbon 6-membered rings. The benzene ring shows the $\pi$-$\pi$ interaction with the $\pi$-electron system in the carbon-based material and shows excellent affinity with the carbon-based material.

Examples of the bonding group to the bio-identifying substance of the linker B are the same as those of the bonding group to the bio-identifying substance of the linker A, and an active ester group is most preferred.

In one or more embodiments, the carbon affinity group and the bonding group to the bio-identifying substance of the linker B may be linked to a group that does not inhibit the affinity and bonding ability of the carbon-affinity group and the bonding group to the bio-identifying substance, and preferably bonded to, for example, a hydrocarbon group, particularly preferably an alkylene group having about 1 to 20 carbon atoms.

The carbon-based material vibrator of one or more embodiments of the present invention may be formed on a transparent substrate such as glass for holding the carbon-based material. When a multi-channel sensor is produced using a vibrator, the vibrator usually has a substrate. However, when the vibrator has a substrate, the vibration energy of the vibrator leaks to the substrate, and the Q value of the vibration is lowered, so that the stability in detection of a biological substance may be lowered. In the case of a graphene vibrator, the vibrator has sufficient strength as a self-supported film and thus can be configured as a vibrator with no substrate. Therefore, the graphene vibrator with no substrate is also preferred.

Next, a method of detecting vibration using the vibrator of one or more embodiments of the present invention will be described. As a method of detecting vibration, a pulse echo method and a resonance method can be adopted.

In one or more embodiments, the pulse echo method is preferably applied to a vibrator having a thickness of more than 500 nm. In the pulse echo method, elastic pulse waves are generated in the vibrator by irradiation of pump light, echoes of the elastic pulse waves repeatedly reflecting inside a thin film are measured, and the attenuation is evaluated from the amplitude of the echoes to measure the vibration displacement of the vibrator. To evaluate the attenuation of the echoes, the vibrator is irradiated with probe light, and a reflectance of the probe light reflected by the vibrator is measured. Then, using a time and a reflectance when the reflectance of the probe light changes, the resonance frequency, the attenuation of the echoes, and the arrival times of the echoes can be determined. When the vibrator detects a biological substance, the apparent thickness of the vibrator increases, the arrival times of the echoes are delayed, and in addition, the amplitude of the echoes decreases since a target protein absorbs the energy of elastic waves. A biological substance can be detected from these changes. Both the pump light and the probe light are preferably laser light, the pulse width of the pump light is preferably on the order of femtoseconds, and the pulse width of the probe light is preferably on the order of femtoseconds.

In one or more embodiments, the resonance method is preferably applied to a vibrator having a thickness of 500 nm or less. In the resonance method, the vibrator is irradiated with ultrashort pulsed light having a pulse width on the order of femtoseconds, a resonance mode with the pulsed light generated in the vibrator by the irradiation is measured from a change in a reflectance of the probe light reflected by the vibrator. By performing Fourier transform on a spectrum in which the horizontal axis indicates time and the vertical axis indicates reflectance of probe light, a spectrum in which the horizontal axis indicates frequency and the vertical axis indicates amplitude can be obtained. From a peak position of this spectrum, a resonance frequency in the vibrator can be determined. When the vibrator detects a biological substance, the resonance frequency (peak position) shifts to low-frequency side, and the biological substance can be detected by the fluctuation of $\Delta f$ the resonance frequency. In addition, since the biological substance absorbs the energy of vibration, the half-width of the resonance peak changes. The biological substance can also be detected by a change in the half-width of the resonance peak.

In one or more embodiments, the specific procedure for detecting a biological substance by applying either the pulse echo method or the resonance method described above to the carbon-based material vibrator of one or more embodiments of the present invention is as follows.

The carbon-based material vibrator of one or more embodiments of the present invention on which a substance having a bio-identifying property is immobilized, is irradiated with pump light from the side opposite to the side on which the substance having a bio-identifying property is immobilized. By the irradiation of pump light, vibration is generated in the vibrator. Then, the vibrator is irradiated with probe light from the side opposite to the side on which the substance having a bio-identifying property is immobilized, and a vibration displacement (change in vibration displacement over time) of the vibrator is detected by either the pulse echo method or the resonance method described above.

After that, when a biological substance to be detected is brought into contact with the vibrator on which the substance having a bio-identifying property is immobilized, the substance having a bio-identifying property reacts with the biological substance to be detected, and a complex of these substances is formed on the surface of the vibrator. With the complex formed on the surface of the vibrator, the vibrator is irradiated with probe light, and a vibration displacement (change in vibration displacement over time) of the vibrator is detected by either the pulse echo method or the resonance method described above. At this time, it is also preferable to measure the vibration displacement in a state where the vibrator is dried after the biological substance to be detected is brought into contact with the vibrator.

Since the above-mentioned complex has a larger mass than the mass of the substance having a bio-identifying property, the total mass of the vibrator and the complex when the complex is formed on the surface of the vibrator is larger than the total mass of the vibrator and the substance having a bio-identifying property.

As a result, the frequency of vibration of the vibrator when the complex is formed on the surface of the vibrator changes from the frequency of the vibrator of one or more embodiments of the present invention on which the substance having a bio-identifying property is formed. By detecting the amount of this change in frequency, a biological substance can be detected.

The carbon-based material vibrator for vibration by light irradiation of one or more embodiments of the present invention is preferably used as a sensor element having the vibrator and a holding member, and such a sensor element is also included in one or more embodiments of the present invention. The sensor element preferably further has a microchannel. The microchannel is a channel through which a specimen flows into the vibrator.

The carbon-based material vibrator of one or more embodiments of the present invention is suitably used in a device of detecting a biological substance, and such a device is also included in one or more embodiments of the present invention. An example of a biological substance detection device of one or more embodiments of the present invention will be described with reference to FIG. 1. A biological substance detection device 100 includes a sensor element 10, a laser light source 110, a half-wavelength plate 111, a polarization beam splitter 112, reflectors 113, 115, 116, and 121 to 123, a corner reflector 114, lenses 118 and 120, an acousto-optic crystal 117, a nonlinear optical crystal 119, a beam splitter 124, a harmonic separator 125, an objective lens 126, and a detector 127. The sensor element 10 includes the vibrator, a holding member, and microchannels 11 and 12, and preferably further includes a substrate of the vibrator.

The laser light source 110 is composed of, for example, a titanium-sapphire pulsed laser, generates pulsed light having a wavelength of 800 nm (pulse width: femtosecond order), and emits the generated pulsed light to the half-wavelength plate 111.

The half-wavelength plate 111 rotates a polarization plane of the pulsed light received from the laser light source 110 by 90° and guides the pulsed light whose polarization plane has been rotated to the polarization beam splitter 112.

The polarization beam splitter 112 transmits the pulsed light received from the half-wavelength plate 111 to the reflector 113 and reflects it in the direction of the lens 118.

The reflector 113 reflects the pulsed light received from the polarization beam splitter 112 to the corner reflector 114.

The corner reflector 114 adjusts the light path of the pulsed light received from the reflector 113 to guide the pulsed light to the reflector 115.

The reflector 115 reflects the pulsed light received from the corner reflector 114 in the direction of the reflector 116.

The reflector 116 reflects the pulsed light received from the reflector 115 in the direction of the acousto-optic crystal 117.

The acousto-optic crystal 117 modulates the pulsed light received from the reflector 116 and emits the modulated pulsed light to the harmonic separator 125.

The lens 118 collimates the pulsed light received from the polarization beam splitter 112 and emits the collimated light to the nonlinear optical crystal 119.

The nonlinear optical crystal 119 converts the pulsed light received from the lens 118 to a doubled frequency light (wavelength=400 nm) and emits it to the lens 120.

The lens 120 guides the pulsed light received from the nonlinear optical crystal 119 to the reflector 121.

The reflector 121 reflects the pulsed light received from the lens 120 in the direction of the beam splitter 124.

The reflector 122 reflects the light received from the reflector 123 in the direction of the detector 127.

The reflector 123 reflects the light received from the beam splitter 124 in the direction of the reflector 122.

The beam splitter 124 separates the pulsed light received from the reflector 121 into two pulsed lights, guides one of the pulsed lights to the harmonic separator 125, and guides the other pulsed light to the detector 127 as reference light. Further, the beam splitter 124 reflects the light received from the harmonic separator 125 in the direction of the reflector 123.

The harmonic separator 125 guides the pulsed light received from the acousto-optic crystal 117 to the objective lens 126, guides the pulsed light received from the beam splitter 124 to the objective lens 126, and guides the reflected light from the sensor element 10 to the beam splitter 124.

The objective lens 126 condenses the light received from the harmonic separator 125 and irradiates the vibrator of the sensor element 10 with the condensed light from the substrate side.

The detector 127 receives the reference light from the beam splitter 124 and receives the reflected light by the sensor element 10 from the reflector 122. Then, the detector 127 subtracts the reference light from the reflected light, inputs the light after the subtraction to a lock-in amplifier, and extracts a modulation frequency component.

The laser light source 110 irradiates the vibrator of the sensor element 10 with a laser light LS1 having a wavelength of 800 nm via the half-wavelength plate 111, the polarization beam splitter 112, the reflector 113, the corner reflector 114, the reflectors 115 and 116, the acousto-optic crystal 117, the harmonic separator 125, and the objective lens 126. This causes vibration in the carbon-based material vibrator of the vibrator. Therefore, the laser light LS1 is called pump light (=excitation light), and the laser light source 110 corresponds to a pump light irradiation means for vibrating the vibrator.

Furthermore, the laser light source 110 irradiates the vibrator of the sensor element 10 with a laser light LS2 having a wavelength of 400 nm via the half-wavelength plate 111, the polarization beam splitter 112, the lens 118, the nonlinear optical crystal 119, the lens 120, the reflector 121, the beam splitter 124, the harmonic separator 125, and the objective lens 126. The reflected light of the laser light LS2 is guided to the detector 127 via the beam splitter 124 and the reflectors 123 and 122. Then, the detector 127 subtracts the reference light from the reflected light of the laser light LS2 to determine acoustic quantities such as the resonance frequency of the vibrator of the sensor element 10. Therefore, the laser light LS2 is called probe light, and the laser light source 110 also corresponds to a means to irradiate the vibrator with the probe light, the vibrator vibrates with the pump light. The detector 127 corresponds to a means to measure a vibration displacement of the vibrator on the basis of the reflectance of the probe light reflected by the vibrator to detect a biological substance.

In the biological substance detection device 100, the detector 127 detects acoustic quantities f0 such as the resonance frequency of the vibrator by the method described above in a state where a solution containing an object to be detected does not flow through the channel 11 of the sensor element 10.

Thereafter, the solution containing an object to be detected flows into a liquid reservoir through the channel 11. Therefore, the channel 11 corresponds to an inflow means of a specimen into the vibrator. The detector 127 detects acoustic quantities fm such as the resonance frequency of the vibrator by the method described above in a state where the solution containing an object to be detected is stored in the liquid reservoir, and detects that the detected acoustic quantities fm such as the resonance frequency have varied from the acoustic quantities f0 such as the resonance frequency, whereby the object to be detected is detected.

As described above, the biological substance measurement device of one or more embodiments of the present invention, including the example shown in FIG. 1, includes (i) the carbon-based material vibrator of one or more embodiments of the present invention, (ii) the holding member of the vibrator, (iii) the microchannel through which a specimen flows into the vibrator, (iv) the pump light source irradiating the vibrator with a pump light to vibrate the vibrator, (v) the probe light source irradiating the vibrator that is vibrated by the pump light with a probe light, and (vi) the detector measuring the vibration displacement of the vibrator on the basis of the reflectance of the probe light reflected by the vibrator to detect a biological substance.

EXAMPLES

Hereinafter, one or more embodiments of the present invention will be more specifically described with reference to Examples. The present disclosure is not limited by the following examples, and can of course be implemented with appropriate modifications within a range that can be adapted to the gist described above and described later, and these are all included in the technical scope of the present disclosure.

The vibrators of the following Example and Comparative Example were evaluated by the following methods.

<Evaluation of Vibration Characteristics of Vibrator>

The produced vibrator was irradiated with a femtosecond pulse laser having an output of 1 mW and a wavelength of 800 nm to excite mechanical resonance in the film thickness direction. The acoustic quantities such as the resonance frequency were measured over time.

<Raman Measurement>

Raman intensity was measured with a laser Raman microscope. The measurement position is not particularly limited, and the measurements were performed at a plurality of positions including one position in the center portion and four positions in the edge portion. The G band intensity (I(G)) and the D band intensity (I(D)) at each position were measured, and the average values thereof were used.

<X-Ray Measurement>

By measuring a reflection spectrum of a graphite film using CuKα as a radiation source, an X-ray reflection (002) diffraction line of the graphite film was used to perform rocking curve measurement.

<Density>

The dimensions and thickness of a carbonaceous film were measured to calculate its volume ($cm^3$), and the mass (g) of the carbonaceous film was separately measured. The density of the carbonaceous film was calculated based on the equation of "density ($g/cm^3$)=mass (g)/volume ($cm^3$)".

Production Example 1: Preparation of Graphite Film

Pyromellitic dianhydride, 4,4'-diaminodiphenyl ether, and p-phenylenediamine were mixed at a molar ratio of 2:1:1 to synthesize 4.0% by mass DMF (dimethylformamide) solution of polyamic acid. The resultant solution was applied onto a copper foil substrate (thickness: 30 μm) using a spin coater. This laminate of the metal foil and the polyamic acid solution was heated at 125° C., 250° C., and 450° C. for 60 seconds each to prepare a polyimide film of 20 mm×20 mm with a thickness of 80 nm. Next, the polyimide film thus formed on the copper foil was peeled off by etching removal of the copper foil, and the polyimide film was sandwiched between graphite sheets, heated to 1000° C. at a rate of 5° C./min in a nitrogen gas atmosphere using an electric furnace, kept at 1000° C. for 5 minutes, and then cooled naturally to obtain an amorphous carbon. The amorphous carbon was sandwiched again between graphite sheets, heated to 2800° C. at a rate of 20° C./min in an argon gas atmosphere, kept at 2800° C. for one hour, and then cooled naturally to obtain a graphite film. At this time, as for the obtained graphite film, the value of I(D)/I(G) in the Raman spectrum was 0.01, the mosaic spread was 0.3°, and the density was 2.2 $g/cm^3$.

Example 1

(1) Vibration Characteristics of Graphite Vibrator

Figure 2:
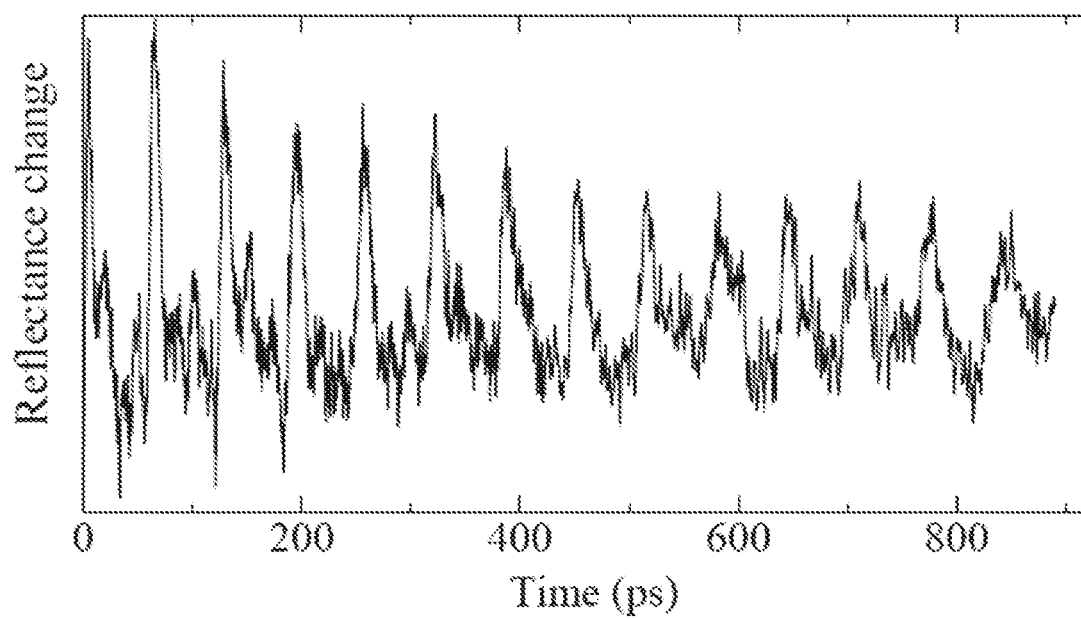
FIG. 2 is a waveform diagram showing a vibration of a graphite vibrator of Example 1 (1).

A graphite film with a thickness of 100 nm was prepared in the same manner as in Production Example 1, and cut into a size of 5 mm×5 mm with a thickness of 100 nm. This graphite film was used as it was as a graphite vibrator. FIG. 2 is a waveform diagram showing the vibration of the graphite vibrator. In FIG. 2, the vertical axis indicates reflectance of probe light, and the horizontal axis indicates time. According to FIG. 2, the vibration continues at an almost constant cycle, and the vibration with sufficient strength can be detected even when more than 800 ps have elapsed. From this, it can be understood that the vibrator has small attenuation and extremely good vibration characteristics.

(2) Biosensor (2-1) Preparation of Graphite Film with Glass Substrate

The graphite film of 15 mm×15 mm with a thickness of 10 nm obtained in Production Example 1 was cut using a YAG laser to obtain a graphite film of 5 mm×5 mm with a thickness of 10 nm. A graphite film with a glass substrate was obtained by dropping a small amount of ethanol on a glass substrate of 10 mm×10 mm with a thickness of 2 mm, floating the graphite film of 5 mm×5 mm with a thickness of 10 nm thereon, and standing it overnight for drying.

(2-2) Preparation of Biosensor 1

The surface of graphite on the glass substrate was washed with oxygen plasma using a plasma etching apparatus manufactured by Harrick Plasma. Next, the graphite film with the glass substrate after washing was immersed in a dimethylformamide (DMF) solution (50 mM) of 1-pyrenebutanoic acid succinimidyl ester (PASE) for 10 hours and then washed with acetone and ultrapure water to immobilize PASE, which serves as a linker with a receptor described later, on the graphite film to obtain a PASE-immobilized graphite film with the glass substrate. Next, an aqueous solution of protein A (100 μg/mL) was added dropwise onto the obtained PASE-immobilized graphite film with the glass substrate, followed by immersion for one hour, to immobilize protein A on PASE, whereby a receptor (protein A)-immobilized graphite film with the glass substrate was obtained. Finally, the obtained receptor-immobilized graphite film with the glass substrate was immersed in an aqueous solution of bovine serum albumin (1 mg/mL), which is an inactive protein, for one hour to block unreacted ester groups of PASE, whereby a biosensor 1 (graphite vibrator) that specifically detects IgG was prepared.

(2-3) Preparation of Biosensor 2 and Vibration Characteristics

A biosensor 2 was prepared in the same manner as in the above (2-1) and (2-2), except that a graphite film having a thickness of 560 nm prepared in the same manner as in Production Example 1 was used. Then, an aqueous solution of rabbit IgG (1 μg/ml) was added dropwise onto the biosensor and allowed to react at room temperature for one hour to specifically bond the rabbit IgG and the above-mentioned protein A. After washing with water, the biosensor was irradiated with laser light from the glass substrate side to evaluate the vibration characteristics. Then, the surface of the biosensor was washed with an aqueous buffer solution of glycine hydrochloride (pH 2.4) to desorb IgG from the protein A. Thereafter, the biosensor was irradiated with laser light from the glass substrate side to evaluate the vibration characteristics.

Figure 3:
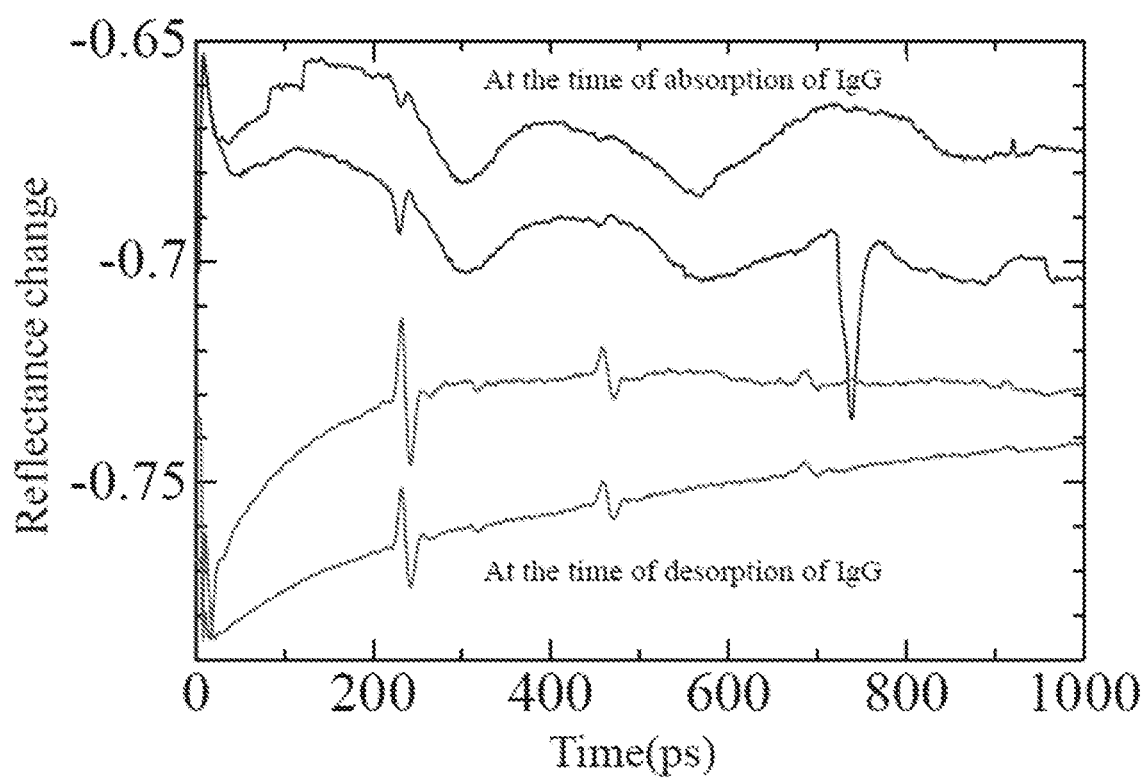
FIG. 3 is a waveform diagram showing vibrations of a biosensor of Example 1 (2).

FIG. 3 is a waveform diagram showing the vibrations of the biosensor 2 composed of a graphite vibrator having a thickness of 560 nm. In FIG. 3, the vertical axis indicates reflectance of probe light, and the horizontal axis indicates time. Even when more than 600 ps have elapsed in the state of desorption of rabbit IgG, and even when 700 ps have elapsed in the state of adsorption of rabbit IgG, the vibration continues at an almost constant cycle, and the vibration with sufficient strength can be detected. From this, it can be understood that the vibrator has small attenuation and extremely good vibration characteristics. In addition, in the state of adsorption of rabbit IgG, the adsorption of rabbit IgG is apparent from the change in the vibration cycle, and this shows that the biosensor was able to detect rabbit IgG with high sensitivity.

Comparative Example 1

Figure 4:
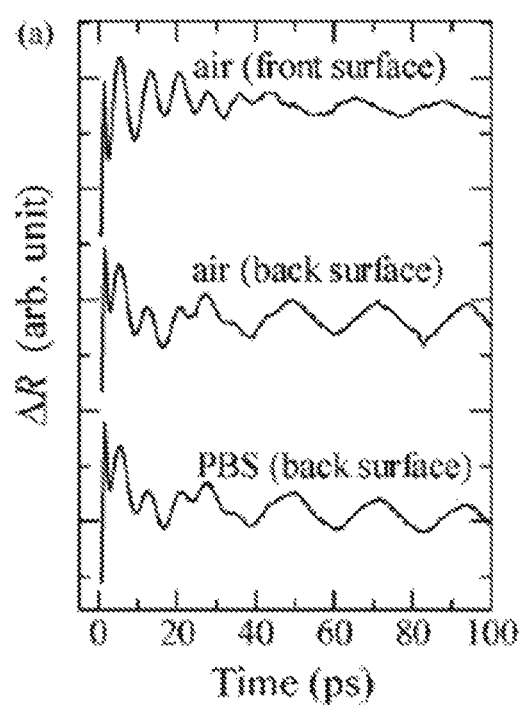
FIG. 4 is a waveform diagram showing vibrations of a Pt vibrator of Comparative Example 1.

A Pt film having a thickness of 50 nm was formed on a substrate to prepare a Pt vibrator with the substrate. FIG. 4 is a waveform diagram showing the vibrations of the Pt vibrator. In FIG. 4, the vertical axis indicates reflectance of probe light, and the horizontal axis indicates time. Among the waveforms as shown in FIG. 4, the two waveforms from the top show the vibrations when only the Pt vibrator with the substrate was allowed to vibrate, and the waveform at the bottom shows the vibration when the Pt vibrator in which SpA (Staphylococcus protein A) was immobilized on the surface of the Pt film, and hIgG was bonded to SpA was allowed to vibrate. According to FIG. 4, the vibrations continue at an almost constant cycle, but the vibrations stop at about 50 ps, and it can be understood that the vibrator is not excellent in detection stability (persistence of vibration).

DESCRIPTION OF THE REFERENCE NUMERALS 10 sensor element
11 microchannel
12 microchannel
100 biological substance detection device
110 laser light source
111 half-wavelength plate
112 polarization beam splitter
113 reflector
114 corner reflector
115 reflector
116 reflector
117 acousto-optic crystal
118 lens
119 nonlinear optical crystal
120 lens
121 reflector
122 reflector
123 reflector
124 beam splitter
125 harmonic separator
126 objective lens
127 detector Although the disclosure has been described with respect to only a limited number of embodiments, those skilled in the art, having benefit of this disclosure, will appreciate that various other embodiments may be devised without departing from the scope of the present disclosure. Accordingly, the scope of the disclosure should be limited only by the attached claims.

The invention claimed is:

1. A carbon-based material vibrator for vibration by light irradiation, wherein a biological substance or a substance capable of identifying a biological substance is immobilized on the vibrator.

2. The carbon-based material vibrator according to claim 1, wherein the carbon-based material vibrator does not comprise a counter electrode for applying a voltage to the carbon-based material vibrator.

3. The carbon-based material vibrator according to claim 1, wherein the carbon-based material is graphite.

4. The carbon-based material vibrator according to claim 3, wherein the graphite has a mosaic spread of 0.1° or more to 3.0° or less.

5. The carbon-based material vibrator according to claim 1, wherein a thermal conductivity $\lambda 1$ in a plane direction of the carbon-based material is 100 times or more than a thermal conductivity $\lambda 2$ in a thickness direction of the carbon-based material.

6. A sensor element comprising the carbon-based material vibrator according to claim 1 and a holder.

7. The sensor element according to claim 6, further comprising a microchannel.

8. A biological substance detector comprising:
the carbon-based material vibrator according to claim 1;
a holder to hold the carbon-based material vibrator;
a microchannel through which a specimen flows into the carbon-based material vibrator;
a pump light source irradiating the carbon-based material vibrator with a pump light to vibrate the carbon-based material vibrator;

a probe light source irradiating the carbon-based material vibrator vibrated by the pump light with a probe light; and a detector measuring a vibration displacement of the carbon-based material vibrator on a basis of a reflectance of a probe light reflected by the carbon-based material vibrator to detect a biological substance.

9. The carbon-based material vibrator according to claim 1, wherein the carbon-based material has a concentration of 2.0 g/cm 3 or more and 2.26 g/cm 3 or less.

10. The carbon-based material vibrator according to claim 1, wherein when the carbon-based material is subjected to laser Raman spectrometry, the ratio of the intensity I(D) of a D band caused by an amorphous carbon structure appearing in 1575-1600 cm$^{-1}$ to the intensity I(G) of a G band caused by a graphite structure appearing in 1350-1360 cm$^{-1}$ is 0 or more to 0.5 or less.

* * * * *